(12) United States Patent
Matsubara et al.

(10) Patent No.: US 8,215,153 B2
(45) Date of Patent: Jul. 10, 2012

(54) GAS SENSOR AND GAS SENSOR UNIT

(75) Inventors: Yoshiaki Matsubara, Nagoya (JP); Takayoshi Atsumi, Konan (JP); Kouji Matsuo, Kasugai (JP); Kazuhiro Kouzaki, Ichinomiya (JP); Masahiro Asai, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 402 days.

(21) Appl. No.: 12/552,360

(22) Filed: Sep. 2, 2009

(65) Prior Publication Data

US 2010/0050740 A1 Mar. 4, 2010

(30) Foreign Application Priority Data

Sep. 2, 2008 (JP) ................................. 2008-225351
Nov. 18, 2008 (JP) ................................. 2008-294959
Jul. 20, 2009 (JP) ................................. 2009-169637

(51) Int. Cl.
*G01N 19/10* (2006.01)
*G01N 7/00* (2006.01)
(52) U.S. Cl. ...................... 73/31.05; 73/23.31; 73/23.32
(58) Field of Classification Search .................... 73/23.2, 73/23.31, 31.05
See application file for complete search history.

(56) References Cited

U.S. PATENT DOCUMENTS

| 5,900,129 | A | 5/1999 | Tsuji et al. | |
|---|---|---|---|---|
| 6,500,322 | B2 * | 12/2002 | Akatsuka et al. | 204/427 |
| 6,679,099 | B2 * | 1/2004 | Fujita et al. | 73/23.2 |
| 7,484,401 | B2 | 2/2009 | Yamauchi | |
| 2006/0101900 | A1 | 5/2006 | Nishio et al. | |
| 2007/0157939 | A1 | 7/2007 | Nakagawa | |
| 2007/0199366 | A1 | 8/2007 | Nishio et al. | |
| 2008/0257016 | A1 * | 10/2008 | Fujii et al. | 73/31.05 |

FOREIGN PATENT DOCUMENTS

| JP | 9-54063 A | 2/1997 |
|---|---|---|
| JP | 2000-249678 A | 9/2000 |
| JP | 2002-181766 A | 6/2002 |
| JP | 2006-145378 A | 6/2006 |
| JP | 2006-162597 A | 6/2006 |
| JP | 2007-147586 A | 6/2007 |
| JP | 2007-155415 A | 6/2007 |
| JP | 2008-111820 A | 5/2008 |
| JP | 2008-139278 A | 6/2008 |
| JP | 2009-168677 A | 7/2009 |

OTHER PUBLICATIONS

Japanese Office Action, dated Dec. 14, 2010, issued in Application No. 2009-169637.

* cited by examiner

*Primary Examiner* — Harshad Patel
*Assistant Examiner* — Punam Roy
(74) *Attorney, Agent, or Firm* — Sughrue Mion, PLLC

(57) ABSTRACT

A gas sensor including a detection element having a detection portion; a metal shell that surrounds the detection element so as to expose the detection portion to a measured atmosphere; an outer tube that is fixed to the metal shell so as to cover a rear end side of the detection element; and a seal member that is contained inside the outer tube, the seal member having a lead wire insertion hole and a through hole that penetrates in the axial direction; a tubular holding member made of a resin having a lower coefficient of thermal expansion than the seal member, the tubular holding member being held inside the through hole, the tubular holding member having a ventilation hole; and a filter that covers the ventilation hole, the filter being joined to the holding member, the filter blocking water from passing therethrough, and the filter having air permeability.

16 Claims, 12 Drawing Sheets

GAS SENSOR AND GAS SENSOR UNIT

BACKGROUND OF THE INVENTION

1. Field of the Invention

The present invention relates to a gas sensor and a gas sensor unit. More specifically, the present invention relates to a gas sensor and a gas sensor unit for detecting the concentration of a specific gas in a measured atmosphere, such as an oxygen sensor, a hydrocarbon sensor, a nitrous oxide sensor, etc.

2. Description of the Related Art

Patent Document 1 discloses a gas sensor in the related art. This a gas sensor includes a plurality of members such as a detection element having a detection portion at a leading end that detects the concentration of a specific gas in a measured atmosphere, a metal shell for holding the detection element so as to expose the detection portion to the measured atmosphere, a tubular shaped outer tube which is fixed to the metal shell so as to cover a rear end of the detection element, and a seal member contained inside the outer tube and having a through hole and lead wire insertion holes. Lead wires are inserted into the lead wire insertion holes for electrically connecting the detection element and external device. The through hole penetrating from the inside to the outside of the outer tube.

In addition, Patent Document 2 also discloses a gas sensor unit in the related art. This a gas sensor unit includes a detection element having a detection portion at a leading end for detecting the concentration of a specific gas in a measured atmosphere, and a gas sensor having sensor terminals electrically connected to the detection portion for sending a signal output from the detection element. In addition, the gas sensor unit also has a sensor cap connected to the gas sensor in order to transmit the output signal from the gas sensor to an external device. This sensor cap has cap terminals electrically connected to the sensor terminals, and an envelopment member which surrounds the cap terminals to form an inside space between the gas sensor and itself. The sensor cap also includes a through hole which allows for communication of the inside space with the outside atmosphere.

Such a gas sensor or gas sensor unit is positioned within an intake manifold or an exhaust manifold of an engine and exposed to the atmosphere intended for measurement. At this time, the gas sensor or the gas sensor unit is exposed to the outside, and therefore water that is splashed by a car may contact the exterior of the gas sensor or the gas sensor unit. As a result, the water can enter the inside of the gas sensor via the through hole. On the other hand, as disclosed in Patent Document 1 or Patent Document 2, a filter for blocking the through hole may be provided. This filter is configured to block water from passing through the through hole. Additionally, the filter has air permeability. Therefore, it can suppress water from entering inside of the gas sensor and simultaneously introduce a reference gas (atmospheric gas) into the gas sensor.

[Patent Document 1] JP-H09-54063-A
[Patent Document 2] JP-2006-162597-A
[Patent Document 3] JP-2008-111820-A

3. Problems to be Solved by the Invention

In the case of the gas sensor disclosed in Patent Document 1 or the gas sensor unit disclosed in Patent Document 2, a rod-shaped filter is directly inserted into the seal member or the sensor cap. Consequently, in order to hold the filter using the seal member or the sensor cap, it is necessary to either press the filter into the seal member or the sensor cap, or hold the filter in place using the elasticity of the seal member or the sensor cap. As a result, the distortion caused by the pressing and elastic holding may reduce the air permeability and negatively impact the effectiveness of the gas sensor.

Alternately, Patent Document 3 discloses a gas sensor having a sheet type filter to block the through hole in the seal member wherein a rear end of the seal member and an outer circumference of the filter are directly fused together along a circumferential direction. In this manner, it is possible to maintain sufficient air permeability of the filter since no pressing or elastic deformation is required. However, when the seal member is deformed by heat generated from an exhausted manifold, the filter cannot track the deformation of the seal member and is thereby torn and peeled away from the seal member. Also, even if the filter could track the deformation of the seal member, there is a problem in that the filter expands and contracts to thereby diminish the air permeability of the filter.

SUMMARY OF THE INVENTION

Therefore, in view of the problems described above, an object of the present invention is to provide a gas sensor and a gas sensor unit capable of suppressing a change in the air permeability of a filter to be maintained by a seal member or an envelopment member. The above object has been achieved in accord with the illustrative aspects of the present invention as set forth below.

According to a first aspect, the present invention provides a gas sensor comprising: a detection element that extends in an axial direction, the detection element having a detection portion that detects a concentration of a specific gas in a measured atmosphere, the detection portion is positioned in a leading end side of the detection element; a metal shell that surrounds the detection element so as to expose the detection portion to the measured atmosphere; an outer tube that is fixed to the metal shell so as to cover a rear end side of the detection element; and a seal member that is contained inside the outer tube, the seal member having a lead wire insertion hole into which a lead wire is inserted for electrically connecting the detection element and an external device and a through hole that penetrates in the axial direction, wherein the gas sensor further comprising: a tubular holding member made of a resin having a lower coefficient of thermal expansion than the seal member, the holding member being held inside the through hole, the holding member having a ventilation hole that introduces a gas into an inside of the outer tube; and a filter that covers the ventilation hole, the filter being joined to the holding member, the filter blocking water from passing therethrough, and the filter having air permeability.

As such, the tubular holding member having the ventilation hole joins the filter in order to cover the ventilation hole, and the holding member is held in the through hole. In this manner, even if the seal member is deformed by heat from the exhaust manifold, the filter is not deformed with the seal member. Further, it is possible to prevent the filter from being torn and altering the air permeability of the filter.

In addition, although the holding member is inserted by pressing it into the through hole of the seal member, or the filter is held by elasticity of the seal member in a state of inserting the holding member into the seal member, it is possible to prevent the filter from becoming distorted and the air permeability thereof from being reduced.

In addition, the holding member is made of resin that has a lower coefficient of thermal expansion than the seal member. Therefore, it is difficult for the holding member to become deformed even though the holding member is heated by the exhaust manifold, and it is possible to prevent the air permeability of the filter from being changed.

Furthermore, in the gas sensor according to the present invention, a temperature of the seal member during use thereof is in a range of about 230° C. to 270° C., and the thermal expansion of the resin rather than the seal member should be suppressed within this temperature range.

In a preferred embodiment of the gas sensor of the first aspect, the filter is welded onto the holding member. Thereby, the filter and the holding member can be tightly joined together.

In addition, the filter may be welded to the outer circumference of the leading end side of the holding member or to the inside of the ventilation hole of the holding member, however, it is preferably welded to the outer circumference of the leading end side of the holding member. This can prevent moisture from remaining inside the ventilation hole of the holding member, thereby obtaining sufficient air permeability. Further, the filter is preferably welded to the entire circumference of the outer circumference of the ventilation hole of the holding member in order to cover the ventilation hole. Thereby, the filter can be tightly fixed to the holding member.

In another preferred embodiment, the gas sensor further comprises a mesh which covers the filter from a rear end side, the mesh being made of metal or a resin having air permeability. In this manner, it is possible to prevent the filter from being torn since the filter is not subject to external impact. Furthermore, the air permeability degree of the mesh is appropriately set but must be greater than that of the filter.

In yet another preferred embodiment, the mesh and the holding member are directly joined to each other by the welding. In this manner, the mesh can be tightly fixed to the holding member. Moreover, the mesh is preferably welded to the entire circumference at a position other than the welding position of the filter and the holding member. In this manner, the mesh can be tightly fixed to the holding member without compromising fixing of the filter and the holding member.

In yet another preferred embodiment, the mesh and the filter are spaced apart from each other. In this manner, the heat during welding is not transferred to the filter when the mesh is directly joined to the holding member by the welding, thus preventing a change in the air permeability degree of the filter due to melting.

In yet another preferred embodiment, the holding member has an outer wall protruding in the axial line direction over a circumference of the outer wall and a depression surrounded by the outer wall, wherein the filter is disposed in the depression and the mesh is joined to the outer wall. In this manner, the filter and the mesh can be surely spaced apart from each other. As such, the heat during welding is not transferred to the filter so as to prevent a change in the air permeability degree of the filter.

In yet another preferred embodiment, the outer wall is provided with protrusions protruding in the axial direction and disposed at a constant interval over the circumference of the outer wall, wherein the mesh is joined to the protrusions. In this manner, it is possible to prevent the mesh from being inclined with respect to the holding member due to the uneven melted and filled amount of the outer wall in the circumferential direction when the outer wall is welded. In other words, by subjecting only the protrusions to welding margins, unevenness in the melted and filled amount of the outer wall in the circumferential direction can be prevented.

In yet another preferred embodiment, the holding member has a concave portion protruding outwardly in a radial direction from the ventilation hole, and the filter and the mesh are nipped in the concave portion. As such, by nipping the filter and the mesh with the holding member, the filter and the mesh can be more tightly fixed to the holding member. Further, as the concave portion, a portion depressed in a radial direction of the ventilation hole from the ventilation hole may be provided. Alternatively, a holding hole that is larger than the ventilation hole is provided in the holding member, the filter and the mesh are disposed in the holding hole, and then the holding hole circumference provided in the vicinity of the holding hole is melted so that it is distorted inwardly in the radial direction, to thereby form the concave portion.

In yet another preferred embodiment, the gas sensor further comprises a covering member that covers the holding member from the rear side so as to cover the filter held by the holding member, and the covering member has the mesh at the position covering the filter. In this manner, the covering member is provided with the mesh independently of the holding member so as to wrap the holding member, thereby easily covering the filter with the mesh.

According to a second aspect, the present invention provides a gas sensor unit comprising: a detection element having a detection portion which detects a concentration of a specific gas in a measured atmosphere, the detection portion being positioned in a leading end side of the detection element; a gas sensor having a sensor terminal which is electrically connected to the detection portion and which transmits a signal output from the detection element; a sensor cap that is combined with the gas sensor, the sensor cap comprising: a cap terminal which is electrically connected to the sensor terminal; and an envelopment member, which surrounds the cap terminal and which is combined with the gas sensor to form an inside space between the gas sensor and the envelopment member, the envelopment member having a through hole so as to establish communication between the inside space and external atmosphere, the sensor cap transmits the output signal to an external device, and wherein the gas sensor unit further comprises: a tubular holding member made of resin having a lower coefficient of thermal expansion than the envelopment member, the holding member being held inside the through hole, and the holding member having a ventilation hole that introduces a gas inside the envelopment member; and a filter that covers the ventilation hole, the filter being joined to the holding member, the filter blocking water from passing therethrough, and the filter having air permeability.

As such, the tubular holding member having the ventilation hole joins the filter in order to cover the ventilation hole, and the holding member is held in the through hole. In this manner, even if the envelopment member is deformed by the heat from the exhaust manifold, the filter does not track the deformation of the envelopment member. Further, it is possible to prevent the filter from being torn or the air permeability of the filter from being changed.

In addition, although the holding member is inserted by pressing it into the through hole of the envelopment member, or the filter is held by the elasticity of the envelopment member in a state of inserting the holding member into the envelopment member, it is possible to prevent the filter from becoming distorted and the air permeability thereof from being reduced.

In addition, the holding member is made of a resin that has a lower coefficient of thermal expansion than the envelopment member. Therefore, the holding member is not subject to deformation even though the holding member is heated by the exhaust manifold, and it is possible to prevent the air permeability of the filter from being changed.

Furthermore, in the gas sensor unit according to the present invention, a temperature of the envelopment member during use thereof is in a range of about 60° C. to 100° C., and the thermal expansion of the resin rather than the envelopment member should be suppressed within this temperature range.

In a preferred embodiment of the gas sensor unit of the second aspect, the filter is welded to the holding member. In this manner, the filter can be tightly fixed to the holding member.

Moreover, the filter may be welded to the inner circumference of the holding member or to the inside of the ventilation hole of the holding member, however, it is preferably welded to the outer circumference of the holding member. This can prevent moisture from remaining in the inside of the ventilation hole of the holding member, thereby obtaining sufficient air permeability. Furthermore, the filter is preferably welded to the entire circumference of the outer circumference of the ventilation hole of the holding member in order to cover the ventilation hole. In this manner, the filter can be tightly fixed to the holding member.

In another preferred embodiment, the gas sensor unit further comprises a mesh that covers the filter from a rear end side, the mesh being made of metal or a resin having air permeability. Thereby, it is possible to prevent the filter from being torn since the filter is not subject to external impact. Further, the air permeability degree of the mesh is appropriately set but must be greater than that of the filter.

In yet another preferred embodiment, the mesh and the holding member are directly joined to each other by the welding. In this manner, the mesh can be tightly fixed to the holding member. Further, the mesh is preferably welded to the entire circumference at a position other than the welding position of the filter and the holding member. In this manner, the mesh can be tightly fixed to the holding member without compromising fixing of the filter and the holding member.

In yet another preferred embodiment, the mesh and the filter are spaced apart from each other. In this manner, the heat during welding is not transferred to the filter when the mesh is directly joined to the holding member by the welding, thus preventing a change in the air permeability degree of the filter due to melting.

In yet another preferred embodiment, the holding member has an outer wall protruding in a penetrating direction of the ventilation hole over a circumference of the outer wall and a depression surrounded by the outer wall, wherein the filter is disposed in the depression, and the mesh is joined to the outer wall. In this manner, the filter and the mesh can be surely disposed spaced apart from each other. As such, the heat during welding is not transferred to the filter so as to prevent a change in the air permeability degree of the filter.

In yet another preferred embodiment, the outer wall is provided with protrusions protruding in the penetrating direction of the ventilation hole and disposed at a constant interval over the circumference of the outer wall, wherein the mesh is joined to the protrusions. In this manner, it is possible to prevent the mesh from being inclined with respect to the holding member due to the uneven melted and filled amount of the outer wall in the circumferential direction when the outer wall is welded. In other words, unevenness in the melted and filled amount of the outer wall in the circumferential direction can be prevented by subjecting only the protrusions to welding margins.

In yet another preferred embodiment, the holding member has a concave portion protruding in a radial direction from the ventilation hole, and the filter and the mesh are nipped in the concave portion. As such, by nipping the filter and the mesh with the holding member, the filter and the mesh can be more tightly fixed to the holding member. Further, as the concave portion, a portion depressed in a radial direction of the ventilation hole from the ventilation hole may be provided. Alternatively, a holding hole larger than the ventilation hole is provided in the holding member, the filter and the mesh are disposed in the holding hole, and then the holding hole circumference provided in the vicinity of the holding hole is melted so that it is distorted inwardly in the radial direction, to thereby form the concave portion.

In yet another preferred embodiment, the gas sensor unit further comprises a covering member that covers the holding member from the rear side so as to cover the filter held by the holding member, and the covering member has the mesh at the position covering the filter. In this manner, the covering member is provided with the mesh independently of the holding member so as to wrap the holding member, thereby easily covering the filter with the mesh.

According to the gas sensor and the gas sensor unit of the present invention, air permeability of the filter is resistant to change, and further can be maintained by the seal member or the envelopment member.

BRIEF DESCRIPTION OF THE DRAWINGS

Illustrative aspects of the invention will be described in detail with reference to the following figures wherein.

DETAILED DESCRIPTION OF THE PREFERRED EMBODIMENTS

The various preferred embodiments of the invention will be described with reference to the drawings. However, the present invention should not be construed as being limited thereto.

First Embodiment

Figure 1:
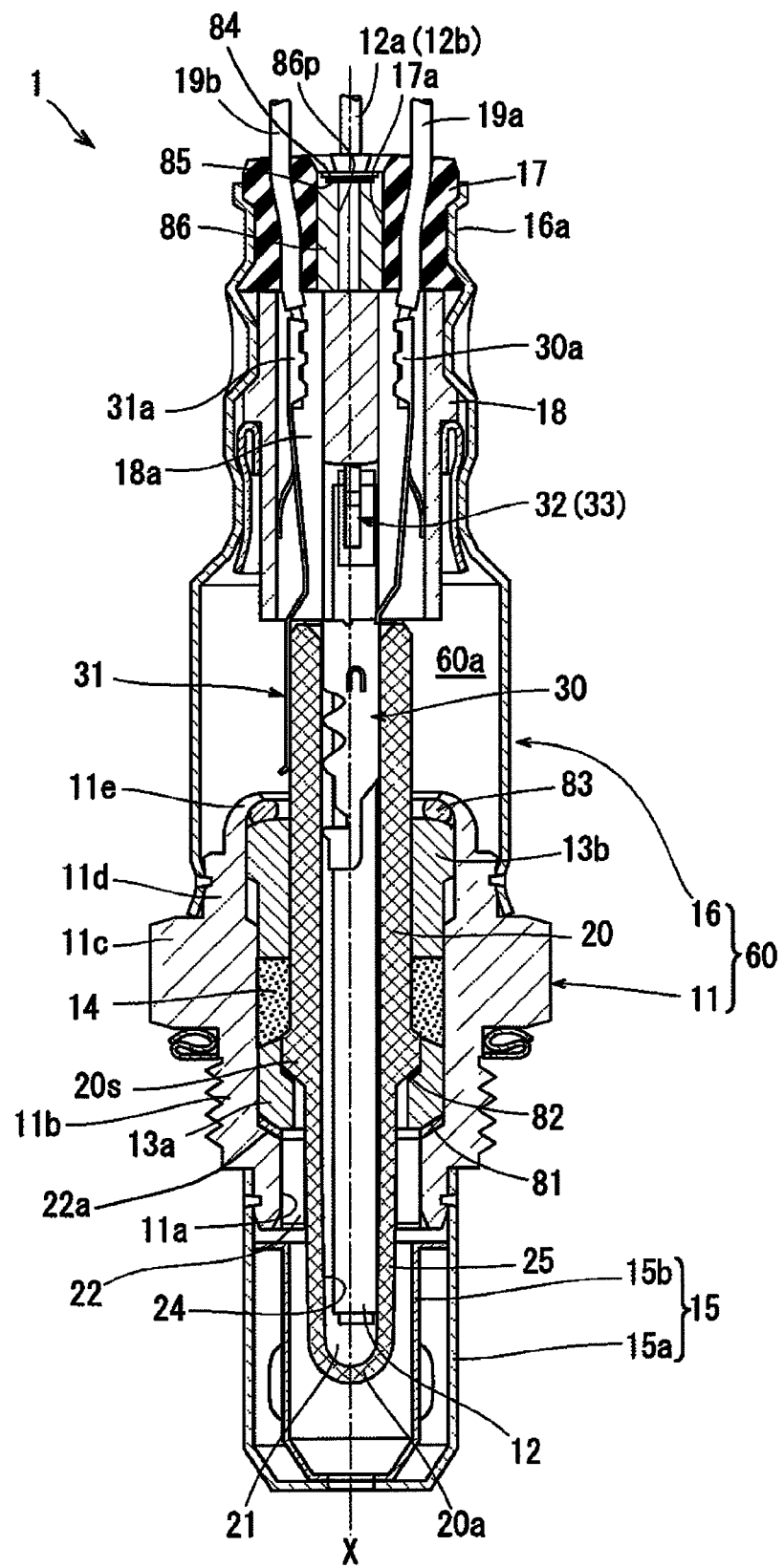
FIG. 1 is a schematic cross-sectional view of a gas sensor 1 according to a first embodiment.
Figure 2:
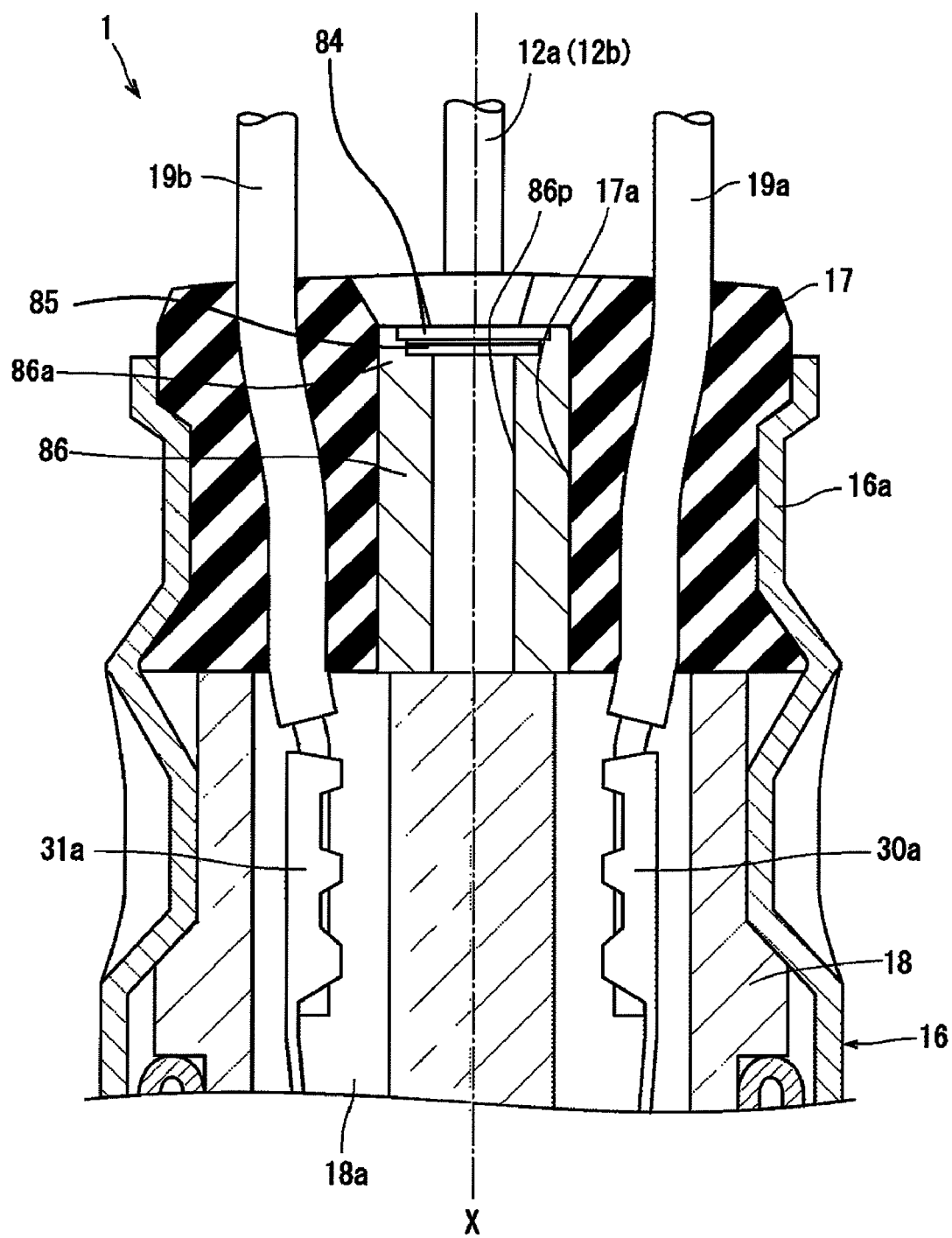
FIG. 2 is an enlarged cross-sectional view of the main components of the gas sensor 1 shown in FIG. 1.

The first embodiment will be described with reference to FIGS. 1 and 2. As shown in FIGS. 1 and 2, a gas sensor 1 according to the first embodiment is, for example, an oxygen sensor, which is equipped in an exhaust system of an automobile and detects oxygen concentration in exhaust gas. The gas sensor 1 includes a detection element 20, a case 60, a seal member 17, a separator 18 and the like.

The detection element 20 is made of a solid electrolyte having oxygen ion conductivity. A leading end of the detection element 20 is closed and a rear end of the detection element 20 is open. The detection element 20 is tubular with a bottom extending axially in an X direction. The leading end of the detection element 20 is provided with a detection portion 20a for detecting oxygen as a measured gas component.

An engagement flange 20s is provided in the middle portion of the detection element 20 in the axial direction and protrudes outwardly in a radial direction. The engagement flange 20s is fixed to a metal shell 11 by interposing a ceramic holder 13a, described below, therebetween. An inner electrode layer 24 is porous and formed by an electroless plating method of a Pt or Pt alloy, for example. The inner electrode layer 24 is disposed on an inner surface of a hole 21 of the detection element 20 in order to cover the entire surface. Additionally, an outer electrode layer 25, which is porous in the same manner as the inner electrode layer 24, is disposed on an entire surface of the leading end side on the surface of the outer circumference of the detection element 20 and followed by the engagement flange 20s. The inner electrode layer 24 is electrically connected to a leading end side of a seal member 30 which is inserted into a rear end side of the hole 21 of the detection element 20. Further, the outer electrode layer 25 is electrically connected to a leading end side of a seal member 31 which is fitted on the outer side of the rear end side of the detection element 20.

In addition, a heater 12 held by the seal member 30 is disposed in the hole 21 of the electrode 20. The heater 12 comes into contact with the surface of the inner circumference of the detection element 20 and activates the detection element quickly by heating the detection portion 20a.

Next, a case 60 is formed by a metal shell 11 and an outer tube 16, the metal shell 11 disposed on the leading end side of the outer tube 16. This case 60 forms a reference gas space 60a in the rear end side of the detection element 20.

Of these, the metal shell 11 is a center-empty tubular body made of metal. The metal shell 11 has a frange 11c protruding outwardly in the radial direction in a substantially central portion along the axial direction thereof and a screw 11b for equipping the gas sensor 1 in the exhaust manifold and disposed in the leading end side followed by the frange 11c. In addition, a leading end side opening 11a is disposed in the leading end side engages a protector 15 and is followed by the screw 11b. On the other hand, a connector 11d for engaging the outer tube 16 is disposed in the rear end side following the frange 11c, and a rear end side opening 11e for crimping is disposed in the rear side following the connector 11d.

The detection element 20 is inserted and disposed in an inner hole 2 of the metal shell 11. The inner hole 2 has a metal part step 22a, and the engagement flange 20s of the detection element 20 is held in the metal part step 22a by interposing a metallic packing 81, a ceramic holder 13a and a metallic packing 82. On the other hand, the rear end side of the engagement flange 20s, in a gap between the metal shell 11 and the detection element 20, is filled with a ceramic powder 14 (e.g., talc), and a ceramic sleeve 13b is also disposed on the rear side of the engagement flange 20s following the ceramic powder 14. The ceramic powder 14 maintaining airtightness by interposing a metallic packing 83 disposed in the rear end side of the ceramic sleeve 13b to crimp the rear end side opening 11e.

The outer tube 16, of which the leading end side is fitted to the connector 11d of the metal shell 11 from the outside, is fixed to the connector by laser welding the entire circumference. In the outer tube 16, the leading end side has a larger diameter than the rear end side, the leading end side surrounds the detection element 20, and a separator 18 and a seal member 17, described below, are disposed in the rear end side.

In addition, the protector 15 is disposed on the leading end side opening 11a of the metal shell 11 so as to cover the detection portion 20a of the detection element 20 protruding from the leading end side opening 11a of the metal shell 11. The protector 15 has a dual structure including an outer protector 15a and an inner protector 15b. Further, a plurality of gas permeation holes for permeating a measured gas is formed in the outer protector 15a and the inner protector 15b. For this reason, the outer electrode layer 25 of the detection element 20 can contact the measured gas through the gas permeation holes of the protector 15.

The separator 18 has a substantially cylindrical body made of insulated alumina ceramic and is disposed between the detection element 20 and the seal member 17, described below. The separator 18 is provided with a cavity 18a having four openings in the rear end surface side of the separator 18, and further, one large opening connected to the four openings in the leading end surface side. A rear end side 30a of the seal member 30 for the inner electrode layer, a rear end side 31a of the seal member 31 for the outer electrode layer and seal members 32 and 33 for heater lead wire (the reference numeral 33 is symmetrically positioned with the reference numeral 32 with respect to the axial line X) are arranged inside the cavity 18a. Further, inside the cavity 18a, the rear end side 30a of the seal member 30 for the inner electrode layer and the rear end side 31a of the seal member 31 for the outer electrode layer are mechanically connected to sensor output lead wires 19a and 19b, described below. Additionally, the seal members 32 and 33 for the heater lead wires are mechanically connected to the heater lead wires 12a and 12b.

The seal member 17 has a substantially cylindrical body made of a fluororubber. The seal member 17 is fitted to the rear end side opening 16a of the metallic outer tube 16 and is sealed in the metallic outer tube 16 by subjecting the rear end side opening 16a to caulking in the radial direction, so that it is disposed in the rear end side of the case 60. A through hole 17a having the axial line X as a center axis is formed in the seal member 17. The seal member 17 as such forms a reference gas space 60a together with the case 60, and the reference gas space 60a communicates with the outside air via the through hole 17a. In addition, the fluororubber used for the seal member 17 of the gas sensor 1 has a $100 \times 10^{-6}/°$ C. to $300 \times 10^{-6}/°$ C. coefficient of thermal expansion.

Also, four lead wire insertion holes are formed in the seal member 17 through which the sensor output lead wires 19a and 19b and the heater lead wires 12a and 12b are pulled outwardly.

Subsequently, main components of embodiments of the present invention will be described. A holding member 86 is inserted in the through hole 17a of the seal member 17. The filter 85 is joined onto a rear end side outer circumference 86a of the holding member 86 by welding. In addition, a mesh 84 is joined onto the rear end side outer circumference 86a of the holding member 86 by welding, in order to cover the filter 85.

Figure 3:
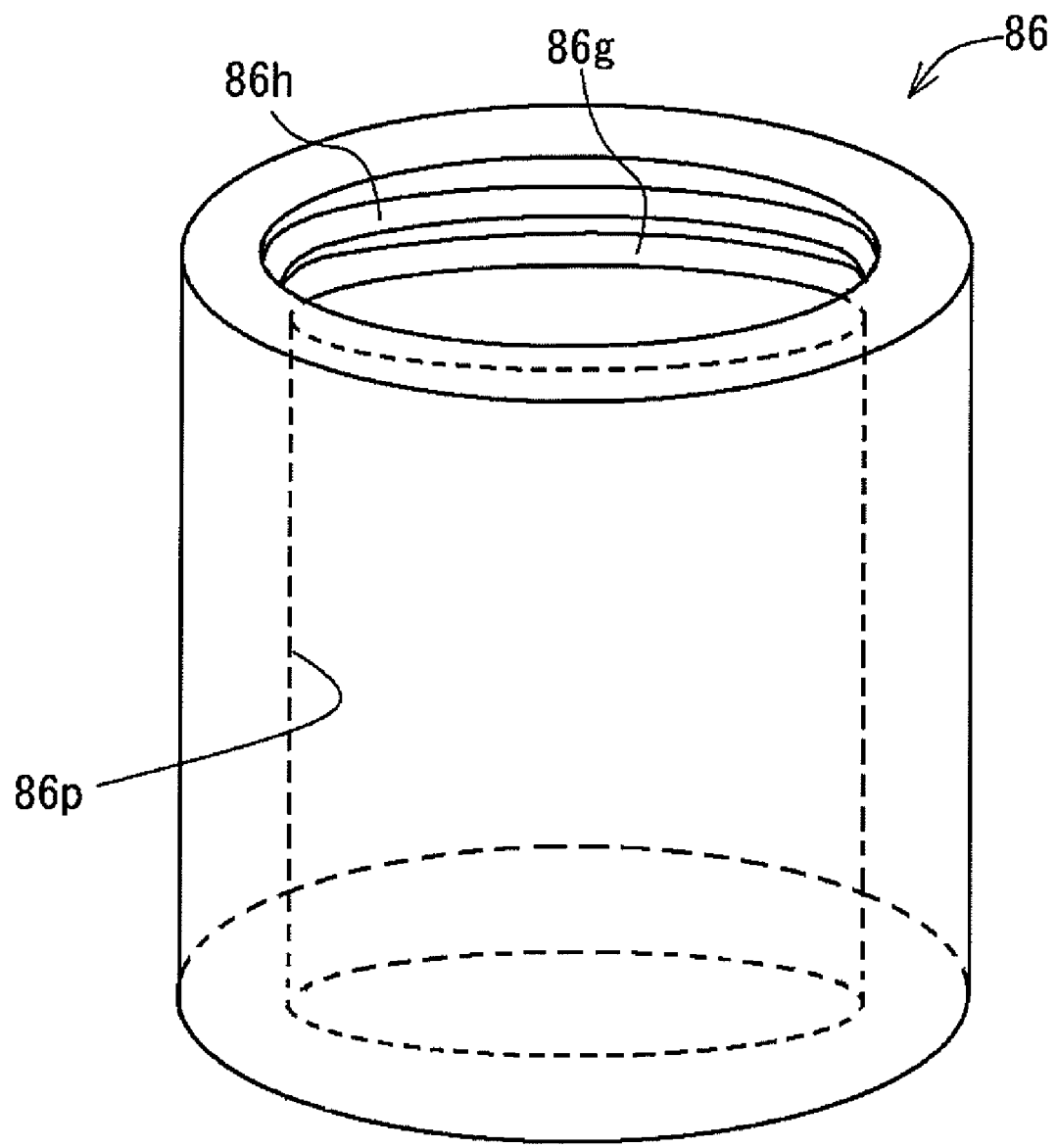
FIG. 3 is a perspective view of a holding member 86.

Of these, the holding member 86 has a ventilation hole 86p toward the rear end side from the leading end side, as shown in FIG. 3. Further, the rear end side outer circumference 86a is provided with a step portion 86g for disposing the filter 85 and a step portion 86h for disposing the mesh 84. The holding member 86 has a lower coefficient of terminal expansion than the seal member 17, and may be made of PPS (poly (phenylene sulfide) resin) or the like. The coefficient of thermal expansion of PPS is $30 \times 10^{-6}/°$ C.

The filter 85 has both water-repellence and air permeability, and is formed of a sheet type PTFE material. The filter 85 is fixed to the holding member 86 and is in contact with the step portion 86g of the holding member 86. The filter 85 is fixed by welding the filter 85 to the holding member 86.

The mesh 84 has a higher air permeability than the filter, and is formed of a net knot using a metal such as stainless steel or the like, or a resin such as PPS or the like. The mesh 84 is fixed to the holding member 86 and is in contact with the step portion 86h of the holding member 86. The mesh 84 is fixed to the holding member 86 by welding the mesh 84 to the holding member 86. In addition, the mesh 84 is fixed to the holding member 86 spaced apart from the filter 85 so as not to contact the filter 85.

As a result of this configuration, the air outside the gas sensor 1 is introduced into the reference gas space 60a in the outer tube 16 through the filter 85 and the ventilation hole 86p of the holding member 86, and furthermore, is introduced into the hole with the bottom 21 of the detection element 20.

The gas sensor 1 of the first embodiment is mounted on, for example, an automobile and the like and is equipped within an intake system manifold or an exhaust system manifold of an engine or the like. Also, the measured gas comes into contact with the outer electrode layer 25 on the outer circumference of the detection element 20 through the gas permeation hole of the protector 15. Further, an electromotive force is generated depending on a difference in oxygen concentration between the air coming into contact with the inner electrode layer 24 and the measured gas. This electromotive force is a detection signal of oxygen concentration in the measured gas. Accordingly, the oxygen concentration in the measured gas can be detected by sending it to an external device through the inner electrode 24, the outer electrode layer 25, the seal member 30 for the inner electrode layer, the seal member 31 for the outer electrode layer and the sensor output lead wires 19a and 19b.

As such, the tubular holding member 86 having the ventilation hole 86p welds the filter 85 in order to cover the ventilation hole 86p, and the holding member 86 is held in the through hole 17a. Thus, even though the seal member 17 is deformed by heat from the exhaust manifold, the filter 85 does not track the deformation of the seal member 17. Consequently, it is possible to prevent the filter 85 from being torn or the air permeability of the filter 85 from being reduced.

In addition, although the holding member 86 is inserted into the through hole 17a of the seal member 17 by pressing, or the filter 85 is held by elasticity of the seal member 17 in a state of inserting the holding member 86 into the seal member 17, it is possible to prevent the filter 85 from being distorted and the air permeability thereof from being reduced.

In addition, the holding member 86 is made of resin that has a lower thermal expansion coefficient than the seal member 17. Therefore, the holding member 86 is resistant to deformation even though the holding member 86 is heated by the exhaust manifold. As such, it is possible to prevent the air permeability of the filter 85 from being changed.

The mesh 84, which is air permeable, is made of metal or a resin. The mesh 84 covers the filter 85 such that it is not subject to external impact. Thus, the mesh 84 may prevent the filter 85 from being torn.

In addition, the mesh 84 and the holding member 86 are joined together by welding, thereby tightly fixing the mesh 84 to the holding member 86.

In addition, to prevent heat from the welding from impacting the filter 85, the mesh 84 and the filter 85 are spaced apart from each other when the mesh 84 is directly welded to the holding member 86, thereby preventing a change in air permeability due to melting of the filter 85.

Second Embodiment

Figure 4:
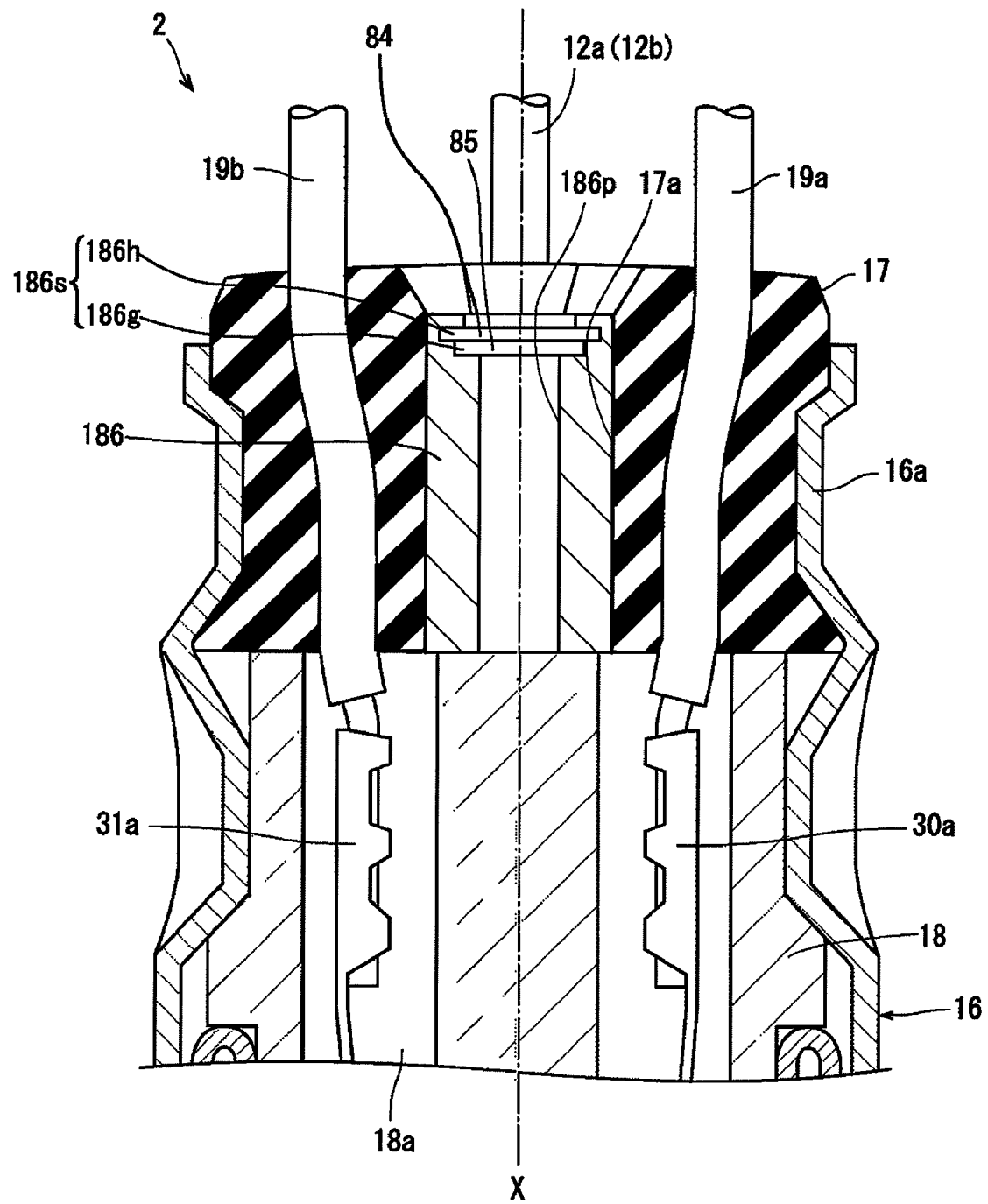
FIG. 4 is an enlarged view of main components of a gas sensor 2 according to a second embodiment.

The second embodiment will now be described with reference to FIG. 4. As shown in FIG. 4, a gas sensor 2 in the second embodiment adopts an insertion member 186 instead of the insertion member 86 of the gas sensor 1 in the first embodiment. The remaining configuration is the same as that of the gas sensor 1 in the first embodiment. Thus, in the second embodiment, the description will be mainly directed to the insertion member 186, and the description of the other components will be made briefly or omitted.

As shown in FIG. 4, the holding member 186 is inserted into the through hole 17a of the seal member 17. The holding member 186 is provided with a ventilation hole 186p toward the rear end side away from the leading end side. Further, a concave portion 186s is provided in the radial direction of the ventilation hole 186p. The concave portion 186s includes a small-diameter concave portion 186g for disposing the filter 85 and a large-diameter concave portion 186h for disposing the mesh 84. The holding member 186 is also made of resin that has a lower coefficient of thermal expansion than the seal member 17 and may be made of PPS (poly(phenylene sulfide) resin) in the same manner as the first embodiment.

The filter 85 is formed of a sheet type material having water-repellence and air permeability using a PTFE material in the same manner as the first embodiment. The filter 85 is fixed to the holding member 186 and is in contact with the small-diameter concave portion 186g of the holding member 186. The filter 85 is fixed by welding the filter 85 to the holding member 186.

The mesh 84 is formed in a net knot shape using a metal such as stainless steel or the like, or a resin such as PPS or the like in the same manner as the first embodiment. The mesh 84 is fixed to the holding member 186 and in contact with the large-diameter concave portion 186h of the holding member 186. The mesh if fixed by welding the mesh 84 to the holding member 186.

Figure 5:
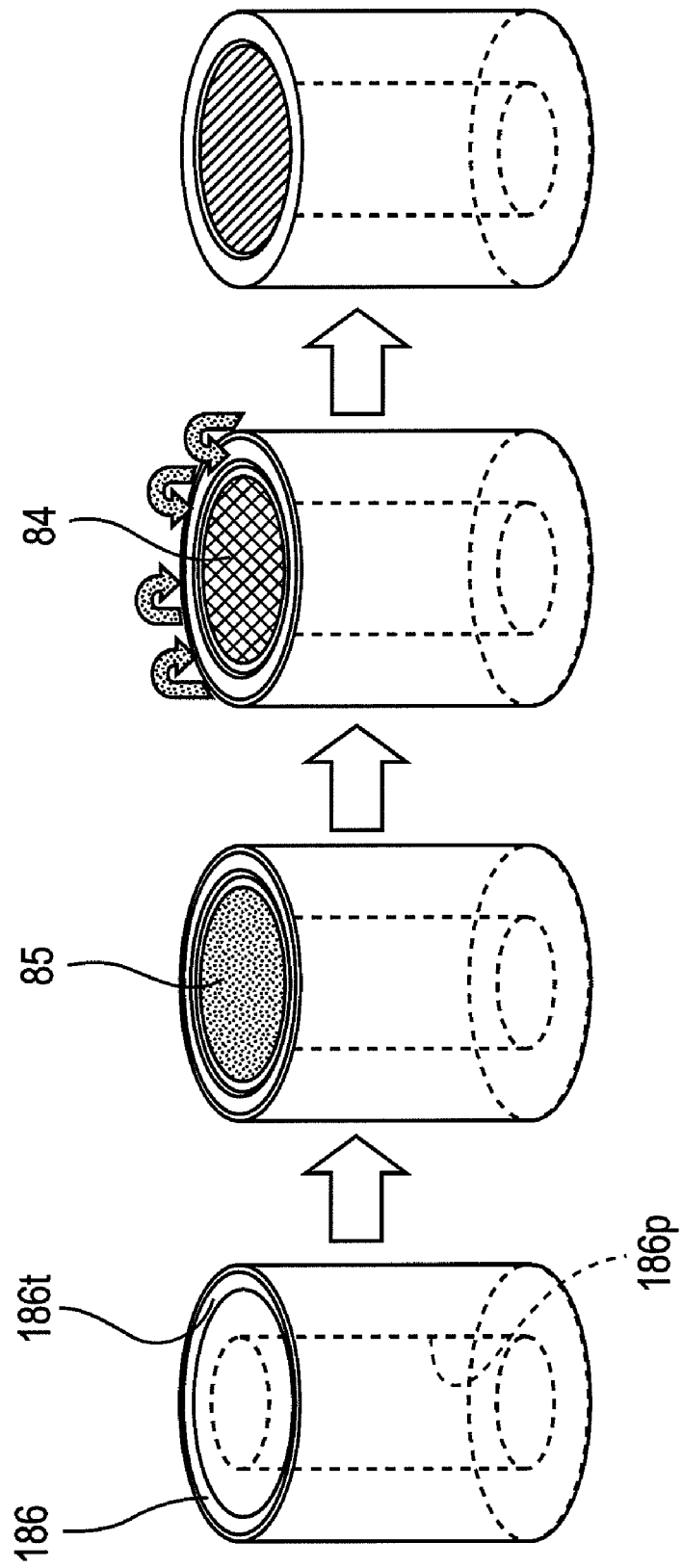
FIGS. 5A to 5D are views illustrating a procedure of equipping a filter 85 and a mesh 84 in the holding member 186 according to the second embodiment.

In addition, in order to fix the filter 85 and the mesh 84 to the holding member 186, as shown in FIGS. 5A to 5D, a holding hole 186t larger than the ventilation hole 186p is provided in the holding member 186 (see FIG. 5A). The filter 85 is disposed in the holding hole 186t and is welded to the holding member 186 (see FIG. 5B). Further, the mesh 84 is inserted and then the holding hole circumference provided in the vicinity of the holding hole 186t is melted so that it is distorted inwardly in the radial direction (see FIG. 5C), to thereby form the concave portion 186s (see FIG. 5D).

As such, the concave portion 186s protruding from the ventilation hole 186p in the radial direction is provided in the holding member 186. In this manner, the filter 85 and the mesh 84 are nipped in the concave portion 186s, so that the filter 85 and the mesh 84 can be more tightly fixed to the holding member 186.

Third Embodiment

Figure 6:
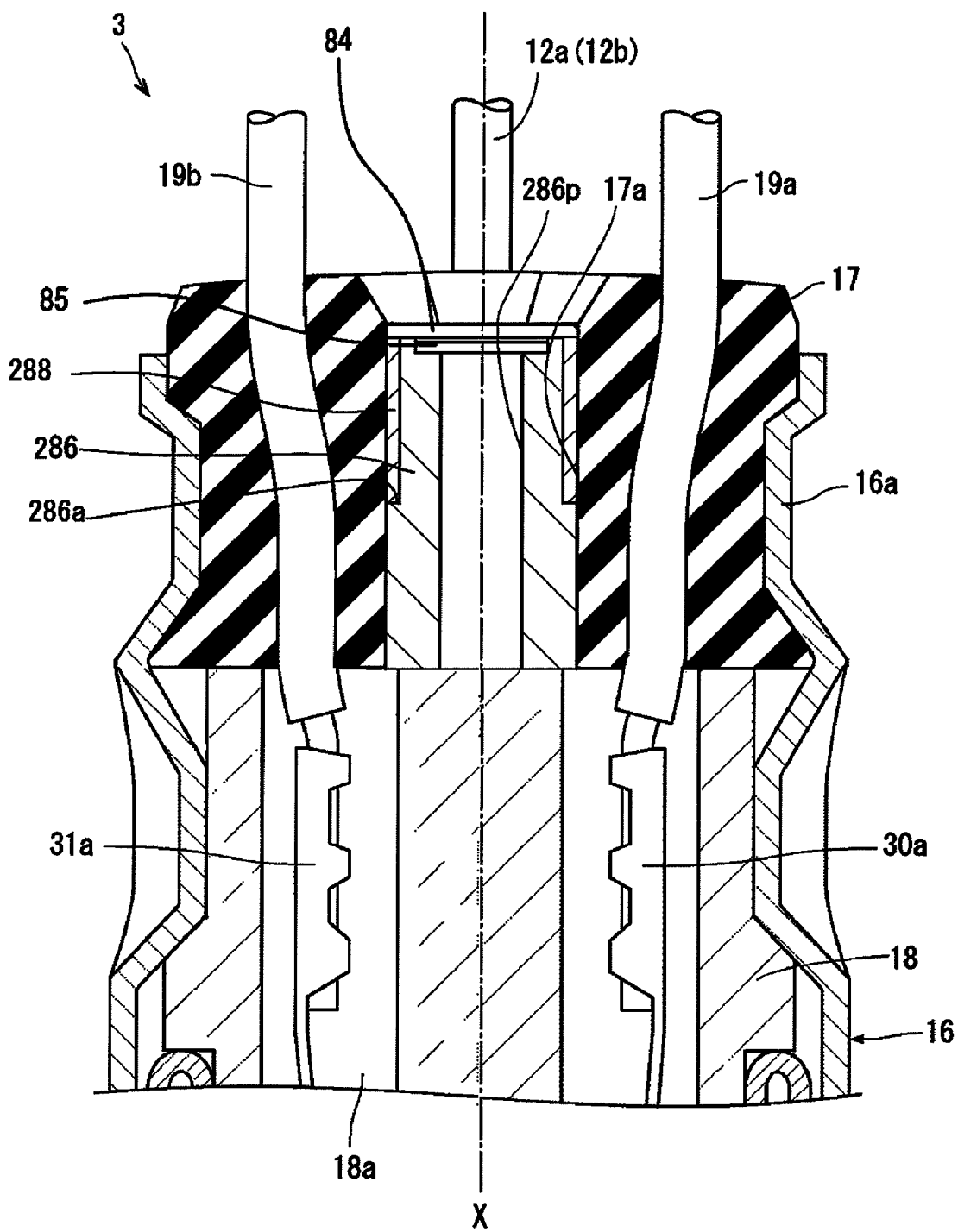
FIG. 6 is an enlarged view of main components of a gas sensor 3 according to a third embodiment.

Next, a third embodiment will be described with reference to FIG. 6. As shown in FIG. 6, a gas sensor 3 in the third embodiment adopts an insertion member 286 and a covering member 288 instead of the insertion member 86 of the gas sensor 1 in the first embodiment. The remaining configuration is the same as that of the gas sensor 1 in the first embodiment. Thus, in the third embodiment, the description will be mainly directed to the insertion member 286 and the covering member 288, and the description of the other components will be made briefly or omitted.

As shown in FIG. 6, the holding member 286 and the covering member 288 are inserted into the through hole 17*a* of the seal member 17. Of these, the holding member 286 is provided with the ventilation hole 286*p* toward the rear end side away from the leading end side. A step portion 286*a* for positioning the covering member 288, described below, is formed on the outer surface thereof. The holding member 286 is also made of a resin that has a lower coefficient of thermal expansion than the seal member 17 and may be made of PPS (poly(phenylene sulfide) resin) in the same manner as the first embodiment.

The filter 85 is formed of a sheet type material having water-repellence and air permeability using a PTFE material in the same manner as the first embodiment. The filter 85 is fixed to the holding member 286 and is in contact with the rear end side outer circumference of the ventilation hole 286*a* of the holding member 286. The filter 85 is fixed by welding the filter 85 to the holding member 286.

The covering member 288 is tubular, enables the mesh 84 to be equipped in the rear end side, and wraps and covers the filter 85 from the rear end side of the holding member 286. The leading end of the covering member 288 comes into contact with the step portion 286*a* of the holding member 286. The mesh 84 is formed of a net knot shape using a metal such as stainless steel or the like, or a resin such as PPS or the like in the same manner as the first embodiment.

In this manner, the covering member 288 wraps the holding member 286 by use of the covering member 288 which is provided with the mesh 84 independently of the holding member 286, thereby easily covering the filter 85 with the mesh 84.

Fourth Embodiment

Figure 7:
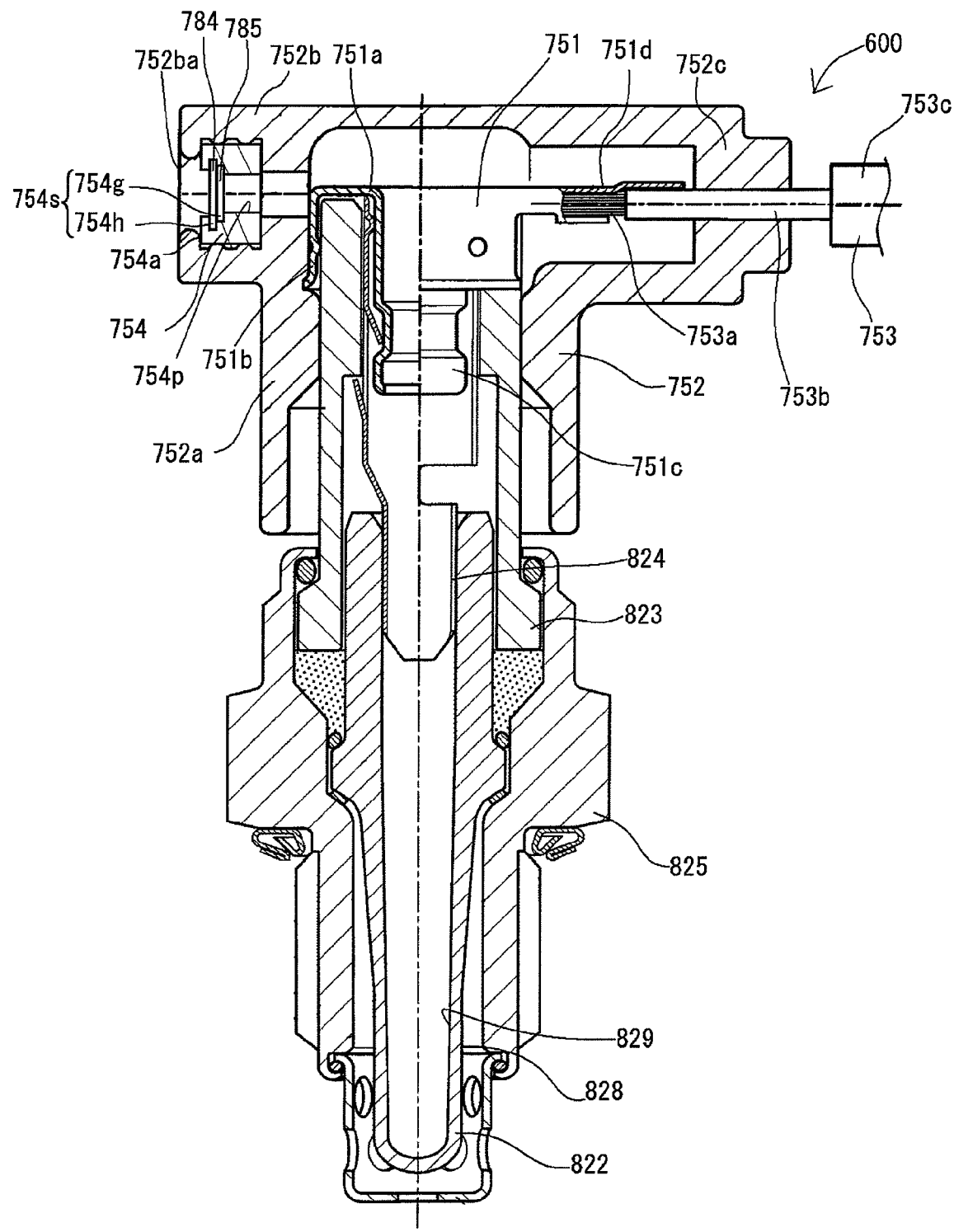
FIG. 7 is an enlarged cross-sectional view of the main components of a gas sensor unit 600 according to a fourth embodiment.
Figure 8:
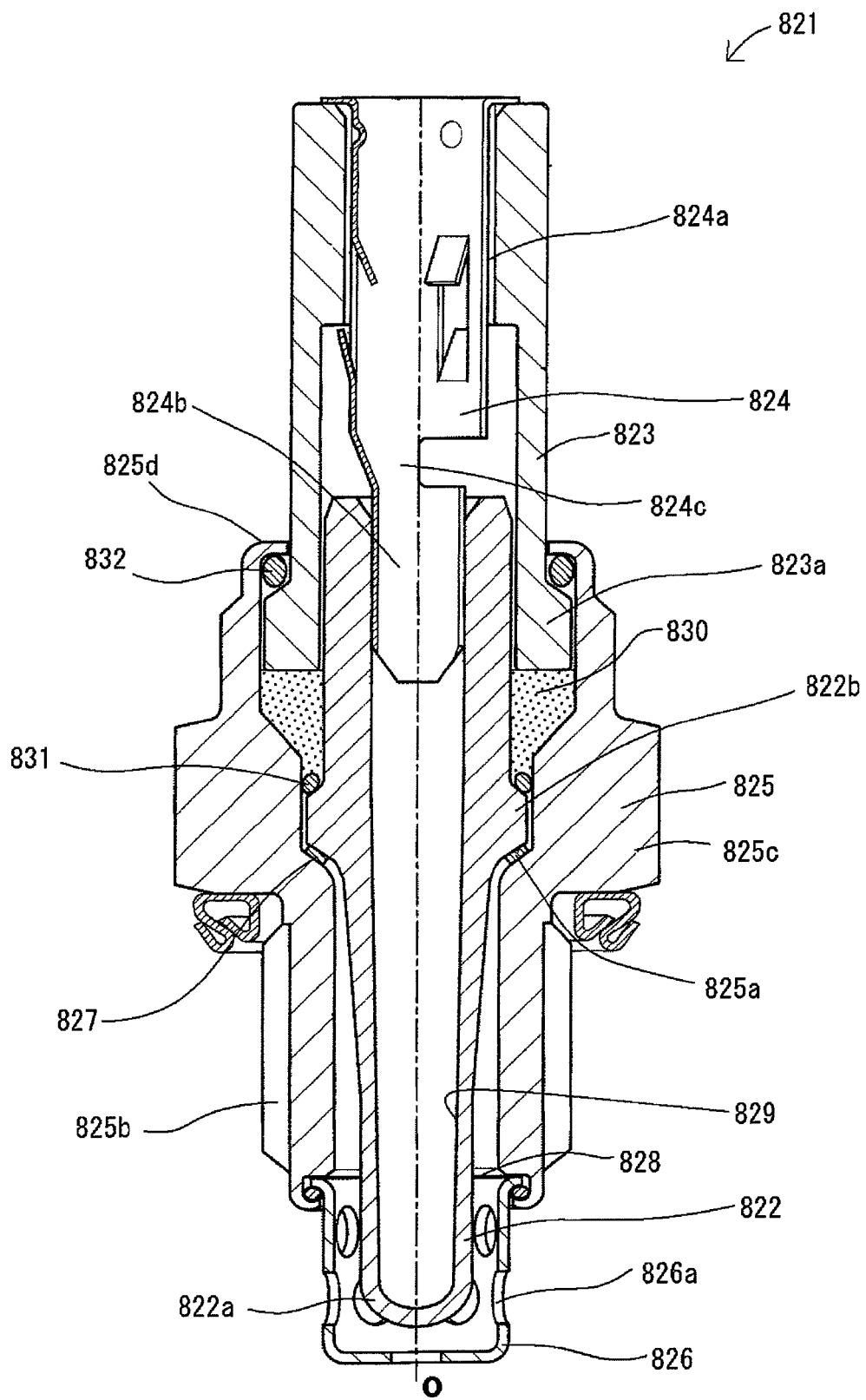
FIG. 8 is an enlarged cross-sectional view of the main components of a gas sensor 800 according to the fourth embodiment.
Figure 9:
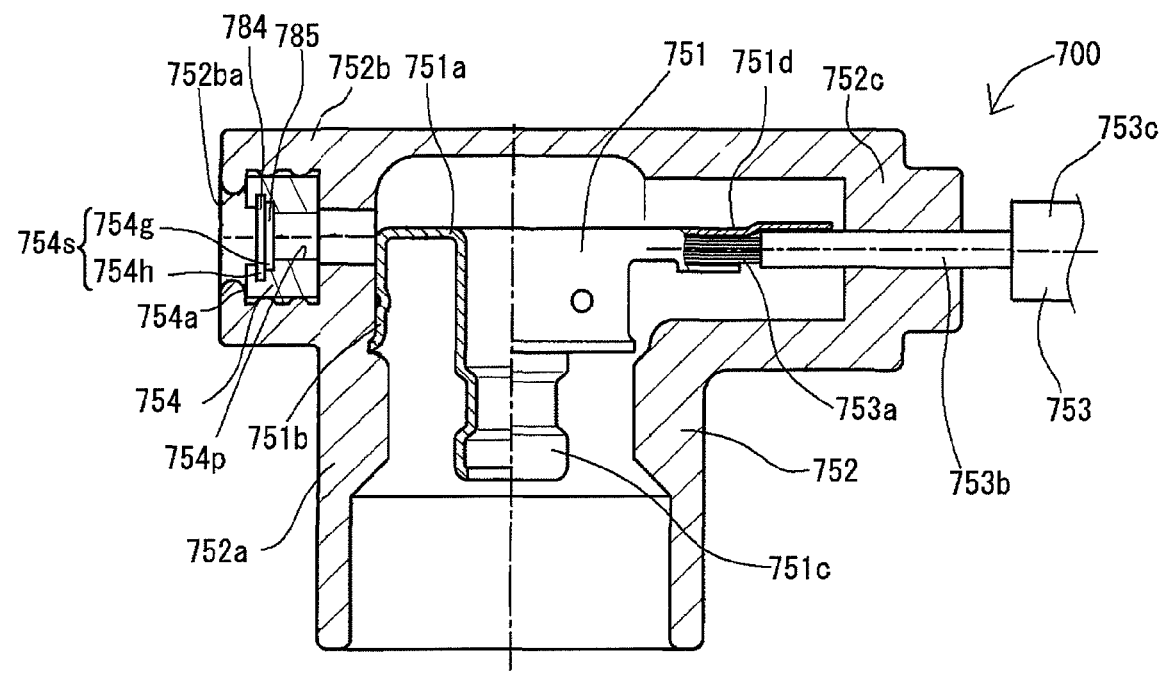
FIG. 9 is an enlarged cross-sectional view of the main components of a sensor cap 700 according to the fourth embodiment.

The fourth embodiment will be described with reference to FIGS. 7 to 9. FIGS. 7 to 9 are diagrams showing a gas sensor unit 600 according to the fourth embodiment. As known from FIG. 7, the gas sensor unit 600 according to this embodiment includes a gas sensor 821 and a sensor cap 700 disposed in the rear end side in the direction of the axial line O of the gas sensor 821. The gas sensor unit 600 is joined to an exhaust manifold of an automobile such that the leading end portion of the gas sensor 821 protrudes into the exhaust manifold. In this embodiment the gas sensor unit 600 is an oxygen sensor for measuring oxygen concentration in an exhaust gas.

The gas sensor 821 includes a gas detection element 822, a ceramic envelopment body 823, a terminal member 824 and a metal shell 825, as shown in FIG. 8.

In addition, hereinafter, in the direction along the axial line O, a mounting direction of the sensor cap is referred to as a rear end side and a direction opposite thereto is referred to as a leading end side.

The metal shell 825 is made of SUS430 and is cylindrical. An inner circumference container 825*a* for supporting a frange 822*b* of the gas detection element 822, described below, is circumferentially arranged in the metal shell 825. The inner container 825*a* is tapered so that it grows thinner toward the leading end side, and protrudes inwardly in the radial direction from the inner circumference. Also, a screw 825*b* for fixing the gas sensor 821 in the exhaust manifold is disposed on the outer side of the metal shell 825, and a hexagonal portion 825*c* which engages an equipment tool for inserting the screw 825*b* into the exhaust manifold is circumferentially arranged in the rear end side of the screw 825*b*. In addition, a protector 826 covering a leading end 822*a* of the gas detection element 822 described below is disposed in the leading end side of the metal shell 825. The protector 826 is made of metal and is configured as a tube body with a cylindrical bottom and has a plurality of gas introduction holes 826*a* for introducing an exhaust gas in the exhaust manifold into the inside of the gas sensor 821.

The gas detection element 822 is made of a solid electrolyte having oxygen ion conductivity. A leading end 822*a* of the gas detection element 822 has a closed bottom and a cylindrical shape with a bottom extending in the axial direction. The outer circumference of the gas detection element 822 is provided with a frange 822*b* protruding outwardly in the radial direction, and the gas detection element 822 is disposed inside the metal shell 825. A metallic packing 827 is interposed between the leading end side surface of the frange 822*b* and the surface of the inner circumference container 825*a* of the metal shell 825. In addition, a representative solid electrolyte making up the gas detection element 822 includes, for example, a solid solution of $Y_2O_3$ and $ZrO_2$, but other solid solutions of oxides of alkaline earth metals or rare-earth metals and $ZrO_2$ may be adopted. In addition, $HfO_2$ may be contained therein.

An outer electrode 828 is disposed on the outer circumference surface in the leading end 822*a* of the gas detection element 822. The outer electrode 828 is a porous Pt or Pt alloy. The outer electrode 828 is provided up to the leading end side surface of the frange 822*b* and is electrically connected to the metal shell 825 through the metallic packing 827. For this reason, a potential of the outer electrode 828 can be extracted from the metal shell 825.

On the other hand, an inner electrode 829 is also disposed in the inner circumference surface of the gas detection element 822. The inner electrode 829 is also a porous Pt or Pt alloy. The ceramic envelopment body 823 is made of insulated ceramic (in detail, alumina) and is cylindrical.

This ceramic envelopment body 823 is crimped by the rear end 825*d* of the metal shell 825 through the metallic packing 832, and is held to be interposed between the gas detection element 822 and the metal shell 825 together with the metallic packing 831 and the ceramic power 830 made of talc. Further, a thicker rear end side portion 823*a* thereof surrounds the circumference of a portion of the rear end side followed by the frange 822*b* of the gas detection element 822.

The terminal member 824 is made of, for example, INCONEL® (Registered Mark, Inconel Corp., England), is tubular, and has an output terminal 824*a*, an element terminal 824*b* and a terminal connector 824*c* for connecting these components.

Of these, the output terminal 824*a* is tubular so that a cross-section orthogonal to the axial line O is substantially C letter-shaped. The output terminal 824*a* is configured to be elastically enlarged in diameter when the ring-shaped portion 751*a* of the cap terminal 751, described below, is moved relative to a direction along the axial line O to be inserted into the output terminal.

On the other hand, the element terminal 824*b* of the terminal member 824 is also tubular so that a cross-section orthogonal to the axial line O is substantially C letter-shaped. This element terminal 824*b* is elastically reduced in diameter and is inserted into the gas detection element 822 so that it is electrically connected to the inner electrode 829. Therefore, for electrical connection, the element terminal 824*b* presses the inner electrode 829 from the inside to the outside in the radial direction.

Subsequently, the sensor cap 700 according to the fourth embodiment will be described with reference to the drawings.

FIG. 9 is a partially broken cross-sectional view of the sensor cap 700. The sensor cap 700 includes a cap terminal 751, an envelopment member 752 covering the cap terminal 751 to hold the same, and a lead wire 753.

The cap terminal 751 is made of, for example, stainless steel (SUS310S or the like) and is formed to be a substantial double cylinder by a plate drawing process. In addition, the cap terminal 751 has a ring-shaped portion 751a which is planar with a concentric ring shape with respect to the axial line O. Further, the cap terminal 751 has a grip portion 751b protruding on one side in a direction along the axial line O and consecutively following the outer circumference of the ring-shaped portion 751a. Also, an insertion portion 751c, which is cylindrical and protrudes in the same direction as the grip portion 751b, consecutively follows the inner circumference of the ring-shaped portion 751a. The ring-shaped portion 751a, the grip portion 751b and the insertion portion 751c are formed as a single body.

When the grip portion 751b of the cap terminal 751 is fitted into the ceramic envelopment body 823 of the gas sensor 821 (see FIG. 7), the insertion portion 751c is inserted into the inside of the ceramic envelopment body 823 and also the inside of the output terminal 824a of the terminal member 824.

In addition, as shown in FIG. 7, the ring-shaped portion 751a comes into contact with the output terminal 824a positioned on the rear end surface of the ceramic envelopment body 823 in a state where the insertion portion 751c is inserted into the output terminal 824a of the terminal member 824, thereby preventing the insertion portion 751c of the cap terminal 751 from being further inserted into the leading end side.

The envelopment member 752 is formed to be center-empty and is insulated with a fluorine-based rubber. The envelopment member 752 contains the cap terminal 751. This envelopment member 75 includes a terminal envelopment 752a having an insertion hole which envelops the cap terminal 751 and the rear end side of the ceramic envelopment body 823 of the gas sensor unit 600. The envelopment member 752 also includes a holding member envelopment 752b provided so as to protrude in the radial direction from the rear end side of the terminal envelopment 752a. The envelopment member 752 also envelops the circumference of the holding member 754 disposed so as to block the through hole 752ba. Further, the envelopment member 752 includes a lead wire envelopment 752c provided so as to protrude in the radial direction from the rear end side of the terminal envelopment 752a, and the lead wire envelopment 752c envelops the circumference of the lead wire 753.

In the terminal envelopment 752a, the rear end side is positioned around the grip portion 751b of the cap terminal 751, the grip portion 751b and the terminal envelopment 752a, such that they come into contact with each other. On the other hand, the leading end side of the terminal envelopment 752a comes closely in contact with the ceramic envelopment body 823 of the gas sensor 821.

Next, the lead wire envelopment 752c will be described. The lead wire envelopment 752c envelops the lead wire 753. The lead wire 753 includes the core wire 753a, and further, a dual coating such as the first coating material 753b and the second coating material 753c. This lead wire 753 is electrically connected to the cap terminal 751. Additionally, the leading end of the core wire is crimped at the core wire crimping portion 751d of the cap terminal 751. In this manner, it is possible to transmit an output signal from the inner electrode 829 of the gas detection element 822 of the gas sensor 821 to an external device (e.g., engine control unit (ECU)) through the lead wire 753.

The holding member envelopment 752b will now be described. The holding member envelopment 752b envelops the circumference of the holding member 754 which is disposed so as to block the through hole 752ba. In addition, the filter 785 is joined by welding to the outer circumference 754a which is exposed to outside of the holding member 754. The mesh 784 is joined by welding to the outer circumference 754a of the holding member 754 in order to cover the filter 785.

Of these, the holding member 754 has a ventilation hole 754p extending toward the inside space from the outside. The outer circumference 754a is provided with a concave portion 754s. The concave portion 754s includes a small-diameter concave portion 754g for disposing the filter 785 and a large-diameter concave portion 754h for disposing the mesh 784. The holding member 754 is made of a resin that has a lower coefficient of thermal expansion than the envelopment member 752 and may be made of PPS (poly(phenylene sulfide) resin).

The filter 785 is formed of a sheet type material having water-repellence and air permeability using a PTFE material. The filter 785 is fixed to the holding member 754 and is in contact with the small-diameter concave portion 754g of the holding member 754. The filter 785 is fixed by welding the filter 785 to the holding member 754.

The mesh 784 has a higher air permeability than the filter 785 and is formed of a net knot shape by using a metal such as stainless steel or the like, or a resin such as PPS or the like. The mesh 784 is fixed to the holding member 754 and is in contact with the large-diameter concave portion 754h of the holding member 754. The mesh 784 is fixed by welding the mesh 784 to the holding member 754.

In addition, the filter 785 and the mesh 784 are fixed to the holding member 754 by the method as shown in FIGS. 5A to 5D in the same manner as the second embodiment.

As such, the filter 785 is welded to the tubular holding member 754 having the ventilation hole 754p in order to cover the ventilation hole 754p. The holding member 754 is held inside the through hole 752ba. In this manner, even though the envelopment member 752 is deformed by the heat from the exhaust manifold, the filter 785 does not track deformation of the envelopment member 752. As such, is possible to prevent the filter 785 from being torn or the air permeability of the filter 785 from being changed.

In addition, although the holding member 754 is inserted into the through hole 752ba of the envelopment member 752 by pressing, or the filter 785 is held by elasticity of the envelopment member 752 in a state of inserting the holding member 754 into the envelopment member 752, it is possible to prevent the filter 785 from being distorted and the air permeability thereof from being reduced.

In addition, the holding member 754 is made of a resin that has a lower coefficient of thermal expansion than the envelopment member 752. In this manner, the holding member 754 is not subject to deformation even though the holding member 754 is heated by the exhaust manifold. As such it is possible to prevent the air permeability of the filter 785 from being changed.

Fifth Embodiment

Figure 10:
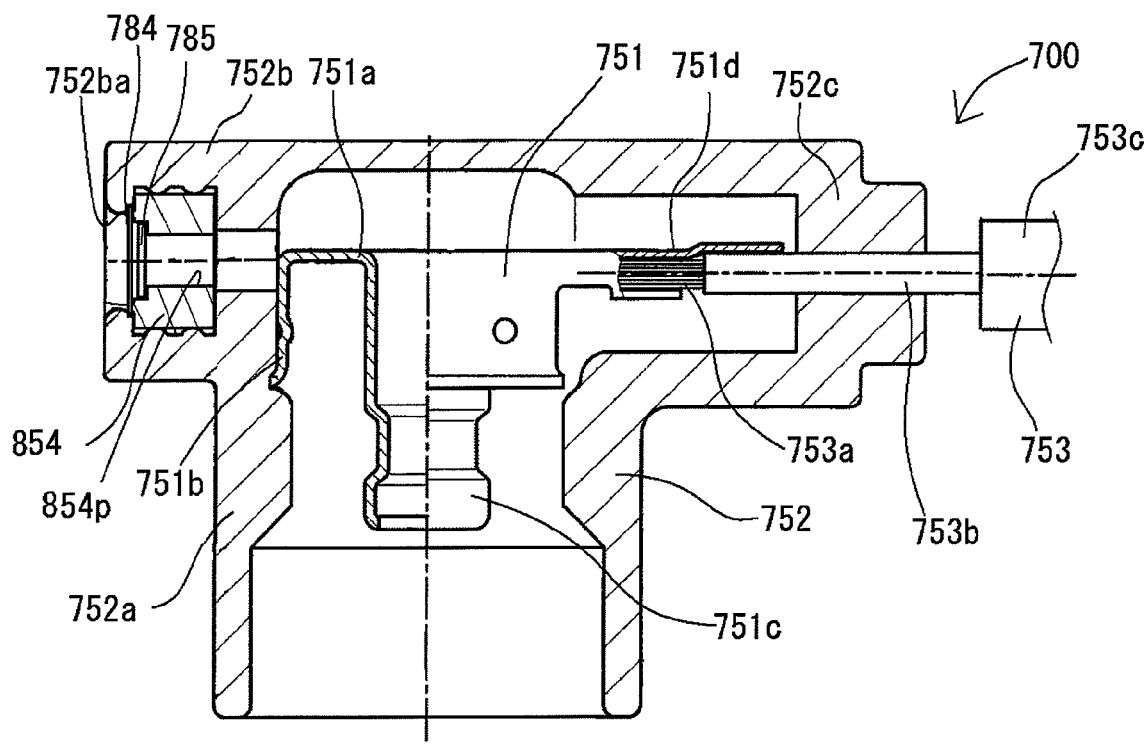
FIG. 10 is an enlarged cross-sectional view of the main components of a sensor cap 700 according to a fifth embodiment.

The fifth embodiment will now be described with reference to FIGS. 10 and 11. A gas sensor unit according to the fifth embodiment adopts a holding member 854 instead of the holding member 754 disposed in the sensor cap 700 of the gas sensor 600 in the fourth embodiment. Otherwise, the remaining configuration is the same as that of the gas sensor unit 600 in the fourth embodiment. Thus, in the fifth embodiment, the description will be mainly directed to the holding member 854, and the description of the other components will be made briefly or omitted.

Next, the sensor cap 700 according to the fifth embodiment will be described with reference to drawings. FIG. 10 is a partially broken cross-sectional view of the sensor cap 700, and FIG. 11 is a perspective view of the holding member 854. The sensor cap 700 includes a cap terminal 751, an envelopment member 752 covering the cap terminal 751 to hold the same, and a lead wire 753 or the like.

The envelopment member 752 is formed to be center-empty, is insulated by fluorine-based rubber and contains the cap terminal 751. This envelopment member 752 includes a terminal envelopment 752a having an insertion through hole which envelops the cap terminal 751 and the rear end side of the ceramic envelopment body 823 of the gas sensor unit 600. The envelopment member 752 also includes a holding member envelopment 752b provided so as to protrude in the radial direction from the rear end side of the terminal envelopment 752a. The holding member envelopment 752b envelops the circumference of the holding member 854 disposed so as to block the through hole 752ba. A lead wire envelopment 752c is provided so as to protrude in the radial direction from the rear end side of the terminal envelopment 752a and enveloping the circumference of the lead wire 753.

Of these, the holding member envelopment 752b envelops the circumference of the holding member 854 disposed so as to block the through hole 752ba. The filter 785 and the mesh 784 are joined by welding to the holding member 854.

Figure 11:
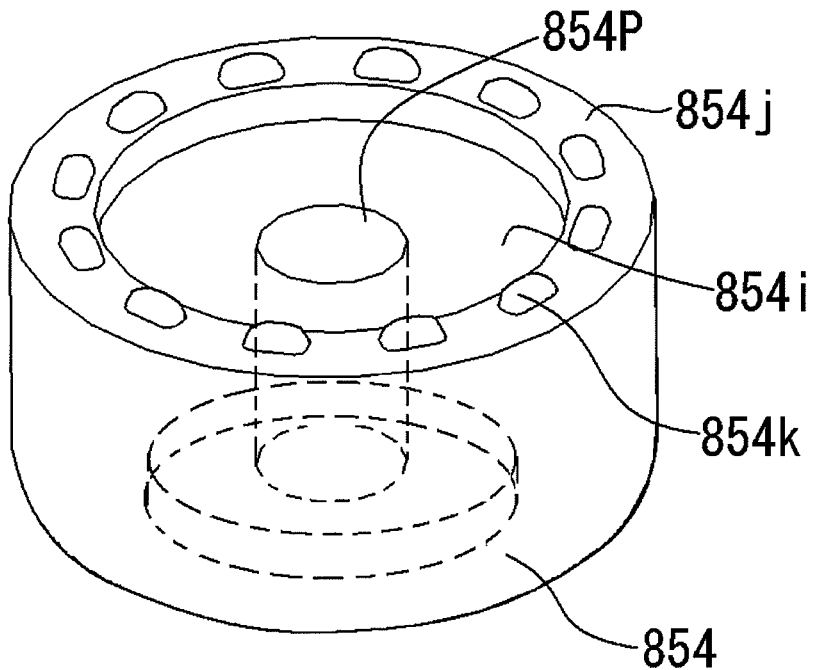
FIG. 11 is a perspective view of a holding member 854 according to the fifth embodiment.

Further, the holding member 854 is made of PPS (poly (phenylene sulfide)resin) and has a ventilation hole 854p extending toward the inside space from the outside as shown in FIG. 11. In addition, a depression 854i for disposing the filter 785 is disposed in the vicinity of the ventilation hole 854p. The filter 785 is disposed and welded in the depression 854i. On the other hand, an outer wall 854j is provided for welding the mesh 784. The outer wall 854j is provided in the vicinity of the depression 854i. Hemisphere protrusions 854k protruding in the axial line direction of the ventilation hole 854p are arranged on the outer wall 854j in the circumferential direction at a constant interval (12 in this embodiment), and the mesh 784 is welded to the protrusions 854k. In addition, to weld the filter 785 and the mesh 784 to the holding member 854, the filter 785 is first disposed in the depression 854i, and the filter 785 is welded to the depression 854i at the heated welding jig (not shown). Thereafter, the mesh 784 is disposed on the protrusions 854k, and the protrusions 854k are melted so that the mesh 784 is welded to the outer wall 854j. In this manner, the filter 785 and the mesh 784 are spaced apart from each other. The opposite side of the depression 854i of the holding member 854 is also concave toward the depression 854i.

As such, the heat induced by welding is not transferred to the filter 785 due to the spacing between the mesh 784 and the filter 785 apart from each other when welding to join the mesh 784 to the holding member 854. This prevents the air permeability from being changed due to melting of the filter 785. In particular, the holding member 854 has the outer wall 854j and the concave portion 854i, the filter 785 is disposed in the depression 854i, and further the mesh 784 is disposed on the outer wall 854j for welding, such that the mesh 784 and the filter 785 are spaced apart from each other. As a result, the heat during the welding is not transferred to the filter 785, thereby preventing the air permeability amount of the filter 785 from being changed. In addition, the protrusions 854k are disposed on the outer wall in the circumferential direction at a constant interval to join the mesh 784 to the protrusions 854k. In this manner, it is possible to prevent the mesh 784 from being inclined with respect to the holding member 854 due to the uneven melting and filling amount of the outer wall 854j in the circumferential direction when the outer wall 854j is welded. In other words, unevenness in the melted and filled amount of the outer wall 854j in the circumferential direction can be prevented by subjecting only the protrusions 854k to welding margins.

Although the present invention has been described in detail and with reference to the above embodiments, the present invention is not limited thereto, and various changes and modifications can be made without departing from the spirit and scope of the invention.

For example, in the first to fifth embodiments, the meshes 84 and 784 are welded to the holding members 86, 186, 286, 754 and 854 in order to cover the filters 85 and 785, However, the present invention is not limited thereto. Specifically, the meshes 84 and 784 may not be used.

In addition, in the first, fourth and fifth embodiments, the meshes 84 and 784 are welded to the holding members 86 and 754 in order to cover the filters 85 and 785. However, the present invention is not limited thereto. Specifically, the meshes 84 and 784 may be fixed to the holding members 86 and 754 by other methods (for example, adhesion by an adhesive, or a nip formed by the holding member and the filter).

In addition, in the fourth and fifth embodiments, the mesh 784 and the filter 785 are welded to the concave portion 754s provided in the holding member 754, respectively, so as to be nipped with the holding member 754, or alternatively, the mesh 784 and the filter 785 are welded to the holding member 854. However, the present invention is not limited thereto. Specifically, the filter 785 may be covered with the mesh 784 using the holding member and the covering member in a manner similar to the third embodiment.

Figure 12:
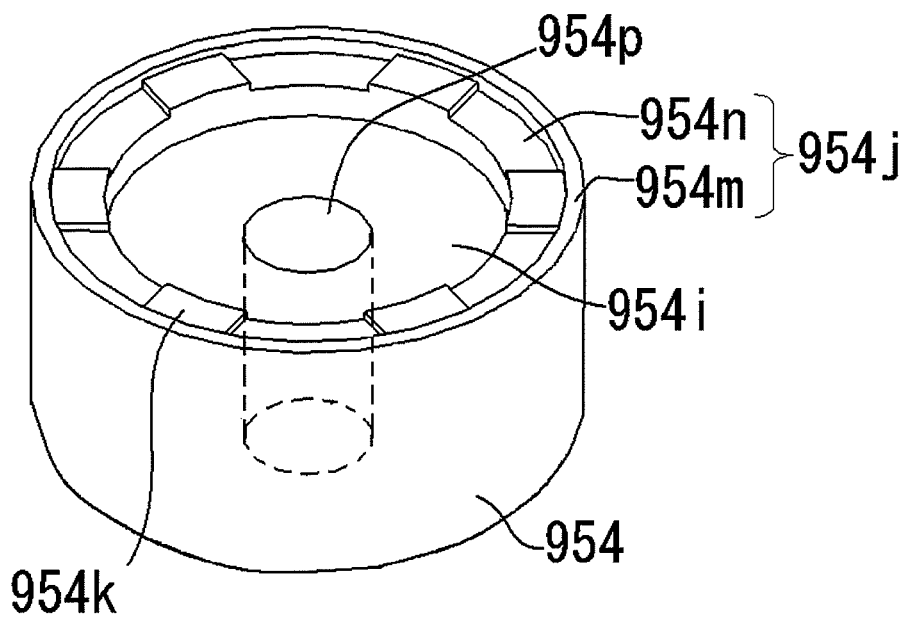
FIG. 12 is a perspective view of a holding member 954 according to a modification.
Figure 13:
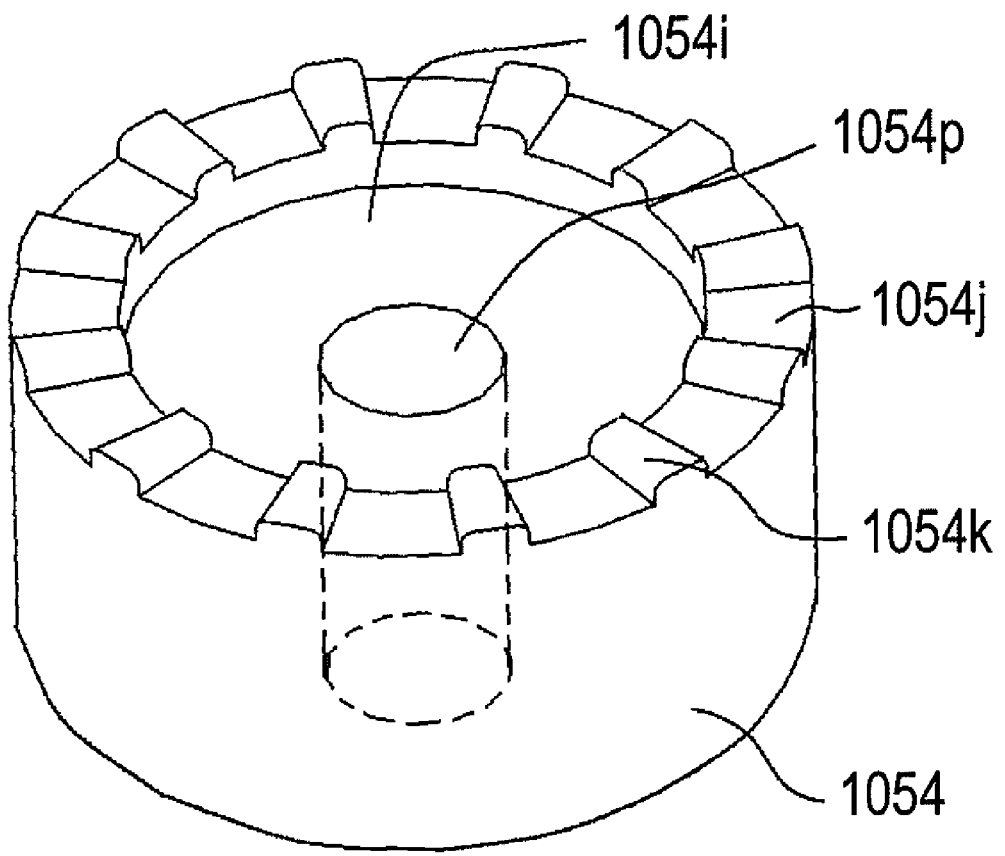
FIG. 13 is a perspective view of a holding member 1054 according to a modification.

In addition, in the fifth embodiment, the holding member 854 having the concave portion 854i and the outer wall 854j has been adopted. However, holding members 954 and 1054 as shown in FIG. 12 or FIG. 13 may be adopted in the fifth embodiment. The holding member 954 shown in FIG. 12 has a ventilation hole 954p toward the inside space from the outside. A depression 954i for disposing the filter 785 is disposed in the vicinity of the ventilation hole 954p. The filter 785 is disposed inside the depression 954i for welding. On the other hand, an outer wall 954j, to which the mesh 784 is welded, is disposed in the vicinity of the depression 954i. Such outer wall 954j has an outermost wall 954m continuing through the circumferential direction, and a step portion 954n which is disposed at an inner side relative to the outermost wall 954m and is formed to be more concave than the outermost wall 954m. Protrusions 954k protruding in the axial line direction of the ventilation hole 954p are arranged on the step portion 954n through the circumference at a constant interval (six in this embodiment). The mesh 784 is welded to the protrusions 954k and is disposed on the outer wall 954j. In addition, the holding member 1054 shown in FIG. 13 is different from the hemispheric protrusions 854k of the holding member 854 shown in FIG. 11 and has protrusions 1054k continuing in the inner surface and the outer surface. This can achieve the same effect as the fifth embodiment.

Further, in the fifth embodiment and the modifications thereof, the holding members 854, 954 and 1054 shown in FIGS. 11 to 13 have been used for the gas sensor unit 600.

However, these holding members 854, 954 and 1054 may be used for the gas sensors 1, 2 and 3 as described in the first to third embodiments.

The present application claims priority from Japanese Patent Application No. 2008-225351, which was filed on Sep. 2, 2008, from Japanese Patent Application No. 2008-294959, which was filed on Nov. 18, 2008, and from Japanese Patent Application No. 2009-169637, which was filed on Jul. 20, 2009, the disclosures of which are incorporated herein by reference in their entirety.

What is claimed is:

1. A gas sensor comprising:
a detection element that extends in an axial direction, the detection element having a detection portion that detects a concentration of a specific gas in a measured atmosphere, the detection portion being positioned in a leading end side of the detection element;
a metal shell that surrounds the detection element so as to expose the detection portion to the measured atmosphere;
an outer tube that is fixed to the metal shell so as to cover a rear end side of the detection element; and
a seal member that is contained inside the outer tube, the seal member having a lead wire insertion hole into which a lead wire is inserted for electrically connecting the detection element and an external device and a through hole that penetrates in the axial direction,
the gas sensor further comprising:
a tubular holding member made of a resin having a lower coefficient of thermal expansion than the seal member, the holding member being held inside the through hole, the holding member having a ventilation hole that introduces a gas into an inside of the outer tube;
a filter that covers the ventilation hole, the filter being joined to the holding member, the filter blocking water from passing therethrough, and the filter having air permeability; and
a mesh that covers the filter from a rear end side, the mesh being made of metal or a resin having air permeability, wherein the mesh has a higher air permeability than the filter.

2. The gas sensor according to claim 1,
wherein the filter is welded onto the holding member.

3. The gas sensor according to claim 1,
wherein the holding member has a concave portion protruding outwardly in a radial direction from the ventilation hole, and
wherein the filter and the mesh are nipped in the concave portion.

4. The gas sensor according to claim 1, further comprising,
a covering member that covers the holding member from the rear end side so as to cover the filter held by the holding member,
wherein the covering member has the mesh at the position covering the filter.

5. The gas sensor according to claim 1,
wherein the mesh and the holding member are directly joined to each other by the welding.

6. The gas sensor according to claim 5,
wherein the mesh and the filter are spaced apart from each other.

7. The gas sensor according to claim 5,
wherein the holding member has an outer wall protruding in the axial direction along its circumference and a depression surrounded by the outer wall,
wherein the filter is disposed in the depression, and
wherein the mesh is joined to the outer wall.

8. The gas sensor according to claim 7,
wherein the outer wall is provided with protrusions protruding in the axial direction and disposed at a constant interval along its circumference, and
wherein the mesh is joined to the protrusions.

9. A gas sensor unit comprising:
a detection element having a detection portion which detects a concentration of a specific gas in a measured atmosphere, the detection portion being positioned in a leading end side of the detection element;
a gas sensor having a sensor terminal which is electrically connected to the detection portion and which transmits a signal output from the detection element;
a sensor cap that is combined with the gas sensor, the sensor cap comprising:
a cap terminal which is electrically connected to the sensor terminal; and
an envelopment member, which surrounds the cap terminal, which is combined with the gas sensor to form an inside space between the gas sensor and the envelopment member, the envelopment member having a through hole which establishes communication between the inside space and external atmosphere,
the sensor cap transmits the output signal to an external device, and
wherein the gas sensor unit further comprises:
a tubular holding member that is made of resin having a lower coefficient of thermal expansion than the envelopment member, the holding member being held inside the through hole, and the holding member having a ventilation hole that introduces a gas inside the envelopment member;
a filter that covers the ventilation hole, the filter being joined to the holding member, the filter blocking water from passing therethrough, and the filter having air permeability; and
a mesh that covers the filter from a rear end side, the mesh being made of metal or a resin having air permeability, wherein the mesh has a higher air permeability than the filter.

10. The gas sensor unit according to claim 9,
wherein the filter is joined to the holding member by welding.

11. The gas sensor unit according to claim 9,
wherein the holding member is provided with a concave portion protruding in a radial direction of the ventilation hole from the ventilation hole, and
wherein the filter and the mesh are nipped in the concave portion.

12. The gas sensor unit according to claim 9, further comprising,
a covering member that covers the holding member from a rear end side so as to cover the filter held by the holding member,
wherein the covering member has the mesh at the position covering the filter.

13. The gas sensor unit according to claim 9,
wherein the mesh and the holding member are directly joined to each other by the welding.

14. The gas sensor unit according to claim 13,
wherein the mesh and the filter are spaced apart from each other.

15. The gas sensor unit according to claim 13,
wherein the holding member has an outer wall protruding in a penetrating direction of the ventilation hole over a circumference of the outer wall and a depression surrounded by the outer wall, wherein the filter is disposed in the depression, and
wherein the mesh is joined to the outer wall.

16. The gas sensor unit according to claim 15,
wherein the outer wall is provided with protrusions protruding in the penetrating direction of the ventilation hole and disposed at a constant interval over a circumference of the outer wall, and
wherein the mesh is joined to the protrusions.

* * * * *